| United States Patent [19] | [11] Patent Number: 4,534,784 |
| Ahle | [45] Date of Patent: Aug. 13, 1985 |

[54] METHOD OF CONTROLLING WEED PESTS

[75] Inventor: James L. Ahle, San Jose, Calif.

[73] Assignee: Stauffer Chemical Company, Westport, Conn.

[21] Appl. No.: 638,078

[22] Filed: Aug. 6, 1984

[51] Int. Cl.³ ............................................. A01N 57/10
[52] U.S. Cl. ........................................................ 71/87
[58] Field of Search ....................................... 71/87, 86

[56] References Cited

U.S. PATENT DOCUMENTS 4,340,416  7/1982  Dutra ...................................... 71/86
4,384,880  5/1983  Large ...................................... 71/87

Primary Examiner—Catherine L. Mills
Attorney, Agent, or Firm—Paul R. Martin

[57] ABSTRACT

A method is disclosed for the pre-emergent control of undesirable weed pests which comprises applying to the locus where control is desired by pre-emergent application of a herbicidally effective amount of the trimethylsulfonium salt of N-phosphonomethylglycine.

6 Claims, No Drawings

METHOD OF CONTROLLING WEED PESTS

BACKGROUND OF THE INVENTION

This invention relates to a method for the control of weed pests using the trimethylsulfonium salt of N-phosphonomethylglycine, a known herbicide.

N-Phosphonomethylglycine and agriculturally acceptable salts thereof are known to be effective herbicides for post-emergent control of various weed species, particularly annual and perennial grasses.

The N-phosphonomethylglycines, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Other methods include the phosphonomethylation of glycine and the reaction of ethyl glycinate with formaldehyde and diethylphosphite. The latter method is described in U.S. Pat. No. 3,799,758 (Franz, Mar. 26, 1974). In addition, there is a whole series of patents relating to N-phosphonomethylglycines, their salts and derivatives thereof, described as being useful herbicides and plant growth regulators. Such additional patents relating to the N-phosphonomethylglycine, methods of application, methods of preparation, salts, and derivatives, include U.S. Pat. No. 3,868,407, U.S. Pat. No. 4,197,254 and U.S. Pat. No. 4,199,354, among others.

The N-phosphonomethylglycines and agriculturally acceptable salts thereof are known to be quite effective in the post-emergent application to weed pests; however, when these compounds are applied in a preemergent manner, it is known that they are tightly bound to the soil and have essentially no pre-emergent activity at nominal rates.

By the term "post-emergent" as used herein, is meant the application of the herbicide to weed pests, after these pests have emerged from the soil. By "pre-emergent" is meant application of the herbicide compound to the soil (PES) or in the soil (PPI) prior to the emergence of the weed pests from the soil as a consequence of growth.

SUMMARY OF THE INVENTION

It has now been discovered that weed pests such as green foxtail, barnyardgrass and shattercane can be effectively controlled by a method which comprises applying the trimethylsulfonium salt of N-phosphonomethylglycine in a pre-emergent manner to the soil at the locus where control is desired.

Accordingly, the method of this invention comprises the application of the trimethylsulfonium salt of N-phosphonomethylglycine to the locus where control is desired.

The method of this invention will be more clearly understood by reference to the following example wherein a comparison was made between various methods of applying the herbicide.

EXAMPLE 1

In this test, a sandy loam soil from the Atpos-Socal area of California was placed in 7×9 inch aluminum trays. Four types of preemergent surface application (PES) or pre-plant incorporated (PPI) treatments were evaluated. These were as follows:

(a) soil seeded, placed in a greenhouse and watered 48 hours before spraying;

(b) soil seeded, covered, placed in a dark growth chamber 48 hours before spraying, not watered;

(c) normal PES (soil planted, sprayed and watered the same day); and (d) normal PPI (soil sprayed, incorporated, seeded and watered the same day).

Formulations were made of the herbicide and application was made at the rate of 25 gallons per acre (gal/A) with two replications each sprayed at 2, 4, and 8 pounds per acre (lb/A) active ingredient (a.i.).

Stock solutions of the trimethylsulfonium salt of N-phosphonomethylglycine were prepared by adding 10.89 grams (g) of the formulated product having 41% active ingredient to 29.11 g of water for a combined total of 40 g.

To apply the active ingredient at the rate of 2 lb/A, 5 milliliters (ml) of this solution were added to 35 ml of water; to apply the active ingredient at the rate of 4 lb/A, 10 ml of the stock solution were added to 30 ml of water; and to apply the active ingredient at the rate of 8 lb/A, 20 ml of the herbicide were added to 20 ml of water.

The weed species against which the herbicide was tested included the following:

| Common Name | Scientific Name | Abbreviation |
| --- | --- | --- |
| annual morning glory | Ipomoea purpurea | AMG |
| sesbania | Sesbania sp. | SES |
| shattercane | Sorghum bicolor | SHC |
| barnyardgrass | Echinochloa crusgalli | BYG |
| annual ryegrass | Lolium multiflorum | ARG |
| green foxtail | Setaria viridis | GF |
| pigweed | Amaranthus retroflexus | PW |

Approximately 15 days after treatment, the aluminum trays were evaluated.

The degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

TABLE I

| | | | Percent Control Ratings | | | | | | |
| --- | --- | --- | --- | --- | --- | --- | --- | --- | --- |
| Compound | Cond. | Rate (lb/A) | AMG | SES | SHC | BYB | ARG | GF | PW |
| TMSG | A | 2 | 0 | 0 | 0 | 50 | 10 | 30 | 0 |
| | | 2 | 0 | 0 | 0 | 40 | 10 | 50 | 0 |
| | | AVG | 0 | 0 | 0 | 45 | 10 | 40 | 0 |
| TMSG | A | 4 | 0 | 0 | 10 | 70 | 0 | 90 | 0 |
| | | 4 | 0 | 0 | 50 | 90 | 20 | 90 | 0 |
| | | AVG | 0 | 0 | 30 | 80 | 10 | 90 | 0 |
| TMSG | A | 8 | 0 | 20 | 90 | 95 | 30 | 90 | 40 |

TABLE I-continued

| Compound | Cond. | Rate (lb/A) | AMG | SES | SHC | BYB | ARG | GF | PW |
|---|---|---|---|---|---|---|---|---|---|
| | | 8 | 0 | 10 | 60 | 90 | 20 | 90 | 10 |
| | | AVG | 0 | 25 | 70 | 93 | 30 | 90 | 25 |
| TMSG | B | 2 | 0 | 0 | 0 | 40 | 10 | 50 | 0 |
| | | 2 | 0 | 0 | 0 | 30 | 0 | 40 | 0 |
| | | AVG | 0 | 0 | 0 | 35 | 5 | 45 | 0 |
| TMSG | B | 4 | 0 | 0 | 10 | 50 | 10 | 80 | 0 |
| | | 4 | 0 | 0 | 10 | 50 | 10 | 70 | 0 |
| | | AVG | 0 | 0 | 10 | 50 | 10 | 75 | 0 |
| TMSG | B | 8 | 0 | 10 | 10 | 30 | 20 | 80 | 30 |
| | | 8 | 0 | 10 | 20 | 80 | 30 | 90 | 30 |
| | | AVG | 0 | 10 | 15 | 55 | 25 | 85 | 30 |
| TMSG | C | 2 | 0 | 0 | 0 | 30 | 10 | 10 | 0 |
| | | 2 | 0 | 0 | 0 | 40 | 10 | 10 | 0 |
| | | AVG | 0 | 0 | 0 | 35 | 10 | 10 | 0 |
| TMSG | C | 4 | 0 | 0 | 20 | 80 | 20 | 70 | 0 |
| | | 4 | 0 | 0 | 10 | 70 | 20 | 70 | 0 |
| | | AVG | 0 | 0 | 15 | 75 | 20 | 70 | 0 |
| TMSG | C | 8 | 0 | 20 | 30 | 70 | 10 | 80 | 10 |
| | | 8 | 0 | 20 | 20 | 80 | 30 | 90 | 20 |
| | | AVG | 0 | 20 | 25 | 75 | 20 | 85 | 15 |
| TMSG | D | 2 | 0 | 0 | 0 | 0 | 0 | 0 | 0 |
| | | 2 | 0 | 0 | 0 | 0 | 0 | 0 | 0 |
| | | AVG | 0 | 0 | 0 | 0 | 0 | 0 | 0 |
| TMSG | D | 4 | 0 | 0 | 40 | 0 | 0 | 0 | 0 |
| | | 4 | 0 | 0 | 40 | 0 | 0 | 0 | 0 |
| | | AVG | 0 | 0 | 40 | 0 | 0 | 0 | 0 |
| TMSG | D | 8 | 0 | 0 | 70 | 20 | 10 | 30 | 0 |
| | | 8 | 0 | 0 | 70 | 10 | 10 | 20 | 0 |
| | | AVG | 0 | 0 | 70 | 15 | 10 | 25 | 0 |

TMSG = Trimethylsulfonium salt of N—phosphonomethylglycine (also known as trimethyl sulfonium N—(phosphonomethyl)glycinate, or trimethyl sulfonium carboxymethylaminomethyl phosphonate)
Condition A: Delayed PES, seeded, covered, placed in greenhouse and watered 48 hours before spraying
Condition B: Delayed PES, seeded, covered with moist soil and placed in dark growth chamber for 48 hours before spraying
Condition C: Normal PES, planted, sprayed and watered the same day
Condition D: Normal PPI, sprayed, incorporated, seeded and watered the same day A review of the results of the foregoing tests demonstrates that the trimethylsulfonium salt of N-phosphonomethylglycine is an effective herbicide against green foxtail, barnyardgrass, and shattercane when applied in a pre-emergent manner.

METHODS OF APPLICATION

The herbicidal compositions of the present invention are useful in controlling the growth of undesirable vegetation by pre-emergence application to the locus where control is desired, including pre-plant soil incorporation as well as surface application. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier.

Their performance is sometimes aided by the inclusion of a wetting agnet, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent are the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anticaking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate composicompositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15-30 mesh.

The surfactant is generally a common wetting agent of anionic or nonionic character. The most suitable wetting agents depend upon the type of granule used. When performed granules are sprayed with active material in liquid from the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granule or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of pre-emergent application can be used. Dusts and liquid compositions can be applied by the use of powder dusters, boom and hand sprayers, and spray dusters. In order to modify or control the growth of germinating seeds, as a typical example, the dust and liquid compositions are applied on the soil surface according to conventional methods and can be distributed throughout the top 3 inches of the soil. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre, and most preferably from about 1 to about 8 pounds per acre, with the actual amount depending on the overall cost and the desired results. It will be readily apparent to one skilled in the art that compositions exhibiting lower herbicidal activity will require a higher dosage than more active compounds for the same degree of control.

What is claimed is:

1. A method for the pre-emergent control of undesirable grass weed pests which comprises applying to the locus where control is desired by pre-emergent application of a herbicidally effective amount of the trimethylsulfonium salt of N-phosphonomethylglycine, said salt being applied at a rate of at least about four pounds per acre.

2. The method of claim 1 wherein said undesirable weed pests are selected from the group consisting of green foxtail, barnyardgrass and shattercane.

3. The method of claim 1 wherein the herbicide is initially applied to the surface of the soil and subsequently incorporated therein to a depth of at least three inches.

4. A method for the pre-emergent control of green foxtail, barnyardgrass and shattercane, which comprises applying to the locus where control is desired by pre-emergent application of an herbicidally effective amount of the trimethylsulfonium salt of N-phosphonomethylglycine, and salt being applied at a rate of at least about four pounds per acre.

5. The method of claim 1 wherein the herbicide is incorporated into the soil to a depth of at least about 3 inches.

6. The method of claim 1 wherein the herbicide is applied as an aqueous solution.

* * * * *